United States Patent [19]
Tomer et al.

[11] Patent Number: 5,900,240
[45] Date of Patent: May 4, 1999

[54] HERBAL COMPOSITIONS AND THEIR USE AS HYPOGLYCEMIC AGENTS

[75] Inventors: Onkar S. Tomer, Watchung; Peter Glomski, South Amboy; Kripanath Borah, Morris Plains, all of N.J.

[73] Assignee: Cromak Research, Inc., Bound Brook, N.J.

[21] Appl. No.: 09/036,317

[22] Filed: Mar. 6, 1998

[51] Int. Cl.⁶ .......................... A61K 35/78; A61K 39/385
[52] U.S. Cl. ......................... 424/195.1; 514/866
[58] Field of Search .......................... 424/195.1; 514/866

[56] References Cited

PUBLICATIONS

Rathi et al. Indian J. Exp. Biol, 19(8), 715–21, 1981.
Karunanayake et al, Journal of Ethnopharmacology 11 (2), 223–31, 1984.
Bailey et al, Diabetes Research 2 (2), 81–4, 1985.
Yoshioka et al, Igaku No Ayumi, 135(3), 241–2, 1985.
Iyer et al. Plant Foods for Human Nutrition, 42(2), 175–82, 1992.
Teixeira et al, Journal of Ethno–Pharmacology 56 (3), 1997.

*Primary Examiner*—Leonard Schenkman
*Attorney, Agent, or Firm*—Jack Matalon

[57] ABSTRACT

An edible composition comprising a mixture of at least two herbs selected from the group consisting of *Syzygium cumini, Gymnema sylvestre, Momordica charantia* and *Solanum melongena*. Preferably, the composition comprises a mixture of *Syzygium cumini* and *Momordica charantia*. A mixture of *Syzygium cumini, Gymnema sylvestre* and *Momordica charantia* is particularly preferred. The herbal mixtures are useful as dietary supplements and are especially useful for lowering the glucose level of the blood in mammals, particularly humans suffering from diabetes mellitus.

12 Claims, No Drawings

5,900,240

HERBAL COMPOSITIONS AND THEIR USE AS HYPOGLYCEMIC AGENTS

FIELD OF THE INVENTION

The invention relates to herbal compositions containing at least two herbs and the use of such compositions as hypoglycemic agents for reducing blood sugar levels in mammals, especially humans, suffering from diabetes mellitus.

BACKGROUND OF THE INVENTION

Diabetes mellitus is an insidious disease for which there is presently no cure. Mammals afflicted with diabetes mellitus will, unless the glucose level in the blood is controlled, ultimately suffer heart attacks, strokes, loss of eyesight, loss of limbs and ultimately may die as the result of this disease.

Humans who suffer from this disease will usually have blood glucose levels in two principal categories, i.e. those who have glucose levels of higher than 150 and are thus termed "insulin-dependent" and those with glucose levels of 110–140 who are termed "non-insulin dependent".

Insulin-dependent diabetics must have insulin administered to them in a very rigorous, disciplined manner and must have snacks between meals since it is necessary to maintain the proper level of insulin in the bloodstream, i.e. undesirable side effects are experienced if the insulin level is too high and the disease will continue unabated if the insulin level is too low. In addition, a disciplined diet is required and if the patient is unwilling or not able to accept insulin injections, pharmaceutical preparations such as "Diabinase", "Orinase", "Glynase", "Glucophage", etc. must be taken. All in all, the insulin-dependent patient is constantly on the narrow edge of either too much or insufficient medication and frequently is not able to tolerate such medication because of its side effects.

The non-insulin dependent diabetes sufferer must follow a disciplined program of diet and exercise to avoid the necessity of taking medication to control blood glucose levels. However, many non-insulin dependent diabetes sufferers experience difficulty in conscientiously following such program and will ultimately fall into the insulin-dependent category sooner or later.

There is a long-felt need for an herbal composition, i.e. a natural, holistic edible composition, which will serve as a hypoglycemic agent and maintain blood glucose levels below the levels obtainable by insulin administration. Such need has especially been true in respect to heavy-set persons as well as those who suffer side effects when taking insulin or synthetic hypoglycemic preparations as well as by those whose life styles are such that they are unwilling or unable to adhere to a rigorous exercise/diet program throughout their lives.

OBJECTS OF THE INVENTION

It is an object of the invention to provide an edible herbal dietary supplement which will be tolerated by insulin-dependent diabetes sufferers without any undesirable side effects and which will allow blood glucose levels to be controlled to a level below that achievable by administration of insulin.

It is a further object of the invention to provide an herbal composition which is relatively inexpensive and in a form which can be readily ingested.

DETAILS OF THE INVENTION

The invention pertains to an edible composition comprising at least two herbs from the following group:

| Botanical Name | Common Name |
| --- | --- |
| Syzygium cumini | Jamun |
| Gymnema sylvestre | — |
| Momordica charantia | Bitter Gourd |
| Solanum melongena | Eggplant |

Preferably, the composition comprises a mixture of *Syzygium cumini* and *Momordica charantia*. A mixture of *Syzygium cumini*, *Gymnema sylvestre* and *Momordica charantia* is particularly preferred.

The ratio of the herbs in the edible composition is not critical, e.g. each herb may be present in amounts as low as 10 wt. %, based on the weight of the composition, with the balance being the other herb(s). However, as a matter of convenience, it is preferable that the composition contain approximately equal amounts of each herb.

Preferably, the compositions contain no fillers or enhancing agents, since such materials are unnecessary and merely serve to dilute the effective concentration of the herbs and to decrease the absorption rate into the blood-stream after ingestion.

The individual herbs are obtained from the sources indicated below and are milled and mixed as dry powders. The dry powder mix may then be further processed into the form of compressed tablets, caplets or lozenges or processed into pouches (i.e. "tea" bags) from which water infusions are ingested.

The preferable method of processing the compositions of the invention for ingestion is to package the powdered herbal mixture into gelatin capsules (preferably hard gelatin) of a size preferably of the order of zero or double zero. Such capsules would then contain about 300–600, preferably about 450, mg of the powdered herbal mixture per capsule. It has been found that hard gelatin capsules represent the most efficient, economical form of packaging of the edible composition of ingestion.

In respect to *Syzygium cumini*, the desired herbal powder is obtained by milling the dry seed kernels in a suitable mill to a fine powder. In respect to *Gymnema sylvestre*, the desired herbal powder is obtained by milling the dried vine along with the dried leaves in a suitable mill to a fine powder. In respect to *Momordica charantia* and *Solanum melongena*, the entire fruits are dried and milled in a suitable mill to a fine powder.

The dosage of the herbal compositions of the invention to be ingested will vary, depending on factors such as severity of the diabetes, age, physical condition and body weight of the patient, diet, etc. As a general guide, it is expected that patients with a body weight in the range of 60–90 kg who are insulin dependent (i.e. blood glucose levels above 150) would ingest about 3,000–5,000 mg/day of the herbal compositions (corresponding to 6–12 zero-size hard gelatin capsules per day) for the first two weeks and thereafter gradually taper off to about 1,500–2,000 mg/day.

It is to be understood that the dosage levels set forth above are only general guides and the proper dosage level for individual patients may vary considerably depending on the indicated above. However, one benefit of the edible compositions of the present invention is that the dosage is not "critical" as is the case with administration of insulin or other hypoglycemic agents consisting of synthetic pharmaceutical medications such as those mentioned above.

Since the edible compositions of the present invention are holistic in nature and represent dietary supplements in their own right, "overdosing" is not a problem. The individual patient with a particular body weight and life style may readily determine the proper dosage by starting out with the general dosage level set forth above and recording the blood glucose level on a daily basis. The patient would then ingest the herbal compositions of the invention in that amount required to maintain a steady state of blood glucose level comparable to and preferably below that achievable by the administration of insulin.

The following non-limiting examples shall serve to illustrate the invention. Unless otherwise indicated, all amounts and parts are on a weight basis.

EXAMPLE 1

Fine powders of *Syzygium cumini*, *Gymnema sylvestre* and *Momordica charantia* were blended in equal amount of each herb and the blended powder was then used to test the hypoglycemic effect in mice. A total of six female mice of strain NON/LtJ was used in this study. This particular strain is specifically used to test for hypoglycemia.

The mice were divided into two groups of three in each group. One group was used as the control and the other group was used to test the effect of the blended herbal powder of the invention. The control group of mice ingested, by demand feeding, 10–15 ml of a 2.5 wt. % glucose solution per day over a period of time of 12 weeks. The test group of mice ingested the same amount of a 2.5 wt. % glucose solution containing 450 mg/l of the solution of the blended herbal powder described above per day over the same period of time.

Blood samples were taken from the tails of each group of mice on a weekly basis and assayed for blood glucose levels using the "One-Touch" glucose meter. The results as shown below in Table I.

TABLE I

Blood Glucose Levels at Indicated Intervals

|  | After 4 weeks | After 8 weeks | After 12 weeks |
|---|---|---|---|
| Control Group | 192 | 174 | 142 |
| Test Group | 175 | 110 | 103 |

As may be seen from Table I, the blood glucose levels of the test group were 30 to 50% lower than those of the control group.

EXAMPLE 2

In this example, a test was made of the hypoglycemic effect of the same herbal powder mixture as employed in Example 1 upon a human being. The test patient was an insulin-dependent diabetic female of 56 years of age and a body weight of 65 kg. The test subject exhibited the daily blood glucose level, with administration of 40 units/day of insulin, measured daily at 8:00 A.M. After 7 days, the subject continued administration of the same number of units of insulin per day and commenced ingestion of 5 size zero hard gelatin capsules containing 450 mg per capsule of the herbal powder mixture of Example 1 per day for a period of 7 days. Thereafter, the subject discontinued administration of the insulin and ingested the 5 size zero hard gelatin capsules containing 450 mg per capsule of the herbal powder mixture of Example 1 per day for 7 days. The results of this test are shown in Table II below.

TABLE II

| Day | Insulin Only | Insulin + Herbal Powder | Herbal Powder Only |
|---|---|---|---|
| 1 | 217 | | |
| 2 | 253 | | |
| 3 | 232 | | |
| 4 | 218 | | |
| 5 | 236 | | |
| 6 | 224 | | |
| 7 | 172 | | |
| 8 | | 223 | |
| 9 | | 178 | |
| 10 | | 190 | |
| 11 | | 183 | |
| 12 | | 200 | |
| 13 | | 210 | |
| 14 | | 180 | |
| 15 | | | 207 |
| 16 | | | 180 |
| 17 | | | 171 |
| 18 | | | 169 |
| 19 | | | 185 |
| 20 | | | 192 |
| 21 | | | 164 |

The results in Table II indicate the dramatic effect of a lowering of blood glucose levels in insulin-dependent human beings to levels lower than those achievable with insulin.

What is claimed is:

1. An edible composition for use as a hyperglycemic agent in mammals comprising 300–600 mg of a mixture of at least three herbs selected from the group consisting of *Syzygium cumini*, *Gymnema sylvestre*, *Momordica charantia* and *Solanum melongena*, each of the foregoing herbs being present in approximately equal amounts.

2. The composition of claim 1 comprising a mixture of *Syzygium cumini*, *Gymnema sylvestre* and *Momordica charantia*.

3. A method for reducing the blood glucose level of a host comprising ingestion by the host of a therapeutically effective amount of the composition of claim 2.

4. The method of claim 3 wherein the host is a non-human animal.

5. The method of claim 3 wherein the host is a human.

6. A method for treatment of diabetes mellitus in a mammal, comprising ingestion by the mammal of a therapeutically effective amount of the composition of claim 2.

7. The method of claim 6 wherein the mammal ingests 2–12 hard gelatin capsules of size 0 or 00 per day, each such capsule containing 300–600 mg of the composition of claim 2.

8. A method for reducing the blood glucose level of a host comprising ingestion by the host of a therapeutically effective amount of the composition of claim 1.

9. The method of claim 8 wherein the host is a non-human animal.

10. The method of claim 8 wherein the host is a human.

11. A method for treatment of diabetes mellitus in a mammal, comprising ingestion by the mammal of a therapeutically effective amount of the composition of claim 1.

12. The method of claim 11 wherein the mammal ingests 2–12 hard gelatin capsules of size 0 or 00 per day, each such capsule containing 300–600 mg of the composition of claim 1.

* * * * *